(12) United States Patent
Adams

(10) Patent No.: US 6,500,451 B2
(45) Date of Patent: Dec. 31, 2002

(54) PROENERGETIC FOOD SUPPLEMENT BASED ON NADH, OCTOCOSANOL AND VITAMIN E

(75) Inventor: Peter Adams, London (GB)

(73) Assignee: World Pharma Tech Ltd., London (GB)

(*) Notice: Subject to any disclaimer, the term of this patent is extended or adjusted under 35 U.S.C. 154(b) by 0 days.

(21) Appl. No.: 09/767,239

(22) Filed: Jan. 22, 2001

(65) Prior Publication Data

US 2002/0009482 A1 Jan. 24, 2002

(51) Int. Cl.⁷ .............................................. A61K 47/00
(52) U.S. Cl. ...................... 424/439; 424/400; 424/464; 424/474
(58) Field of Search ................................ 424/400, 439, 424/469, 474

(56) References Cited

U.S. PATENT DOCUMENTS 5,332,727 A * 7/1994 Birkmayer ................. 424/94.1

FOREIGN PATENT DOCUMENTS

IT           0 561 745 A2 *  2/1993  ............. A23L/1/03

* cited by examiner

Primary Examiner—Thurman K. Page
Assistant Examiner—Charesse Evans
(74) Attorney, Agent, or Firm—Notaro & Michalos P.C.

(57) ABSTRACT

The object of this invention is a food supplement based on NADH, Octocosanol and Vitamin E, which stimulates the generation of energy by the organism.

4 Claims, No Drawings

PROENERGETIC FOOD SUPPLEMENT BASED ON NADH, OCTOCOSANOL AND VITAMIN E

The object of this invention is a food supplement based on NADH, Octocosanol and Vitamin E, which stimulates the generation of energy by the organism.

NADH (nicotinamide adenine dinucleotide in a reduced form) is a physiological substance found in all living cells including human cells as an activating factor of various enzymes which catalyze oxidation and reduction reactions. In particular, the prime function of NADH is to stimulate cell breathing activity, while using up oxygen to form water and three molecules of ATP, an energy-rich compound available in all living cells.

NADH triggers the production of energy by generating ATP, and acts as a primary activating enzyme capable of controlling the oxidation and reduction mechanisms of the cells' metabolic processes.

NADH is an extremely complex molecule and an essential element in drawing energy from foodstuffs. NADH is therefore a prime electron carrier in the oxidation of molecules generating energy within the cell. The greater the content of NADH in the cell, the greater the energy is produced.

As the most powerful antioxidant present in the body, NADH is capable of rigenerating other important antioxidants meant to protect the body at against the attack of free radicals. A few molecules of NADH can have a powerful effect on the body's anti-oxidizing defenses against free radicals causing disease.

The lack of NADH translates to an energy deficiency on a cellular level, and its relative symptom is tiredness. Unfortunately, the NADH level found in the human body drops with age, and the same happens to the enzymes depending on NADH, in particular to those destined for producing energy.

NADH is found in all living cells, animal or vegetable. It is consequently also found in our daily food intake. Meat, poultry and fish contain the highest share of NADH. Vegetables, fruit and other vegetarian food have a much lower NADH content than meat. It should be noted that the major portion of the NADH absorbed with the food is destroyed by cooking. The situation would not be much improved even if our diets consisted of raw meat or fish, as most of the NADH found in these foodstuffs is destroyed by the gastric juices present in the stomach.

The foremost biological functions of NADH are as follows:

1. As a cellular fuel for generating energy,
2. As a key role player in regulating the cell and repairing DNA,
3. As a stimulator of the cellular immunity system,
4. As a powerful antioxidant,
5. As a stimulator of dopamine, adrenaline and noradrenaline.

Octocosanol is also present in the food supplement of this invention.

Octocosanol is a natural food element found in small quantities in vegatable oils and waxes, in alfalfa leaves, wheat and other germs.

The mechanism by which Octocosanol performs a marked ergogenic action (generating work or liberating energy) is not fully understood and is the subject of further studies.

The food supplement of this invention also contains Vitamin E.

Vitamin E is well known to exhibit antioxidant properties, which occur in the cell to protect a, number of important biological compounds from oxidation, such as the polyunsaturated fatty acids, Vitamin A, the carotenes, etc. It is particularly found in legumes and vegetable oils.

It has now been discovered that if NADH is associated with Octocosanol there is a surprising boost of the NADH's ergogenic activity, and further that the addition of Vitamin E happens to have a stabilizing action on the NADH, so as to render the same less vulnerable to degradation.

The object of this invention is therefore a food supplement based on NADH, Octocosonol and Vitamin E, which may be utilized for stimulating the organism to generate energy under conditions of physical tiredness, in sports practices and/or in any situation expected to cause an expenditure of energy.

In particular, the NADH is present in the food supplement of this invention in a quantity of 1–15% by weight of the total, and preferably of 3–7% by weight of the total.

The Octocosonol is present in the food supplement of this invention in a quantity of 1–15% by weight of the total, and preferably of 3–7% by weight of the total.

The Vitamin E is present in the food supplement of this invention in a quantity of 2–15% by weight of the total, and preferably of 6–13% by weight of the total.

The food supplement of the invention may also eventually contain some amino-acids, such as adenosine in a quantity of 15% by weight, and other vitamins such as Beta Carotene oxidation inhibitor, in a quantity of about 5% by weight, and nicotinamide, a forerunner of NADH, in a quantity of about 10% by weight.

The food supplement may also contain some anti-oxidants and anti-radicals, such as grape extract, powdered red wine, resveratrol, lycopene, bioflavonoids from citrus fruit, alpha lypoic acid, carotenoids, selenium yeast, ubidecarenon (Q10 enzyme activator), dry whortleberry extract, reduced glutatione, dry sea pine barl extract, apple vinegar, dry gree tea extract, dry elder tree extract, and antocyanines from red oranges. Said anti-oxidants and anti-radicals may be present in the food supplement in a quantity of about 20–30% by weight, while the yeast is present at a level of about 150 mcg.

The association of NADH with Octocosanol turns out to be an important active energy deliverer as it was found in the reactions in vitro that were carried out in laboratory.

The Vitamin E addition turns out to be important for its anti-oxidizing and stabilizing effects on the NADH, as shown in the laboratory tests specified hereunder (see TEST FOR THE STABILIZING ACTIVITY OF VITAMIN E ON NADH).

The product described above may be administered with the addition of appropriate vehicles and in a variety of pharmaceutical forms such as hard or soft capsules or tablets. Because of the high instability of NADH, the preferred pharmaceutical form is that of a tablet coated with a gastrointestinal barrier, so as to be capable of overcoming the acidity of the stomach and of being absorbed at an intestinal level.

In order to produce this gastrointestinal barrier, it is for instance possible to use an acid copolymer free of isopropanol and methacrylates which is applied over the tablets mass by a suitable apparatus known as a rotating conditioner.

The rotating conditioner induces a cascading motion of the mass of tablets to be coated, during which the mass is wetted by a liquid holding the coating material in solution.

A current of air then allows the material to dry out. This achieves a first light protective layer; alternating wetting and drying phases complete the entire protective processe. Once the gastrointestinal protective coating is applied, the product is sampled and 10 tablets are immersed in an acid solution (at pH 4) at a constant temperature of 32 degrees C.

The tablets must remain intact for at least 90 minutes, the protection is otherwise inadequate, requiring a further coating step.

If the tablets exceed the threshold of 90 minutes, a countercheck is performed by immersing the 10 pills in a basic solution (at pH 7), at a constant temperature of 32 degrees C. The tablets must then dissolve within a time of 15–20 minutes.

A few non-limiting examples of formulations of this invention and of the test for evaluating the stabilizing activity of Vitamin E on NADH follow.

TEST FOR THE STABILIZING ACTIVITY OF VITAMIN E ON NADH

Two beakers are prepared containing 50 g of water at a pH 4 and a constant temperature of 32° C.

10 mg of NADH are dissolved in the first beaker and agitate. The effect of the acidity deactivates the NADH, which splits up into AND+H. Within 20 minutes, 9.5 mg of NADH are split-up, while 0.5 mg remain unchanged.

In a second beaker 20 mg of NADH and 5 mg of Vitamin E are dissolved. The effect of the acidity deactivates the NADH, which splits up into AND+H. Within 20 minutes, 7.5 mg of NADH are split-up, while 2.5 mg of NADH remain unchanged.

The parameters of pH 4 and 32° C. for a duration of 20 minutes has been chosen as the food supplement is to be assumed in the morning on an empty stomach, 30 minutes before breakfast. This leads the tablets to easily pass the physiological stomach barrier in 20 minutes, so as reach the first portion of the intestine, where it can be absorbed and enter the blood circulating system.

| EXAMPLE OF A FORMULATION 1 FOR TABLETS OF 80 MG/CMP | |
|---|---|
| NADH | 2.5 mg |
| OCTOCOSONOL | 2.5 mg |
| VITAMIN E | 5 mg |
| VEGETABLE MAGNESIUM STEARATE | 3 mg |
| MICROCRYSTALLINE CELLULOSE | 41 mg |
| SIPERNAT (HYDRATED SILICA) | 1 mg |
| DIBASIC CALCIUM PHOSPHATE | 25 mg |

| EXAMPLE OF A FORMULATION 2 FOR TABLETS OF 80 MG/CMP | |
|---|---|
| NADH | 5 mg |
| OCTOCOSONOL | 5 mg |
| VITAMIN E | 10 mg |
| VEGETABLE MAGNESIUM STEARATE | 3 mg |
| MICROCRYSTALLINE CELLULOSE | 31 mg |
| SIPERNAT (HYDRATED SILICA) | 1 mg |
| DIBASIC CALCIUM PHOSPHATE | 25 mg |

| EXAMPLE OF A FORMULATION 3 FOR TABLETS OF 80 MG/CMP | |
|---|---|
| NADH | 5 mg |
| OCTOCOSONOL | 2.5 mg |
| Q10 ENZYME ACTIVATOR | 20 mg |
| VEGETABLE MAGNESIUM STEARATE | 2.4 mg |
| MICROCRYSTALLINE CELLULOSE | 37 mg |
| SIPERNAT (HYDRATED SILICA) | 2.6 mg |
| DIBASIC CALCIUM PHOSPHATE | 10.5 mg |

| EXAMPLE OF A FORMULATION 4 FOR TABLETS OF 80 MG/CMP | |
|---|---|
| NADH | 5 mg |
| VITAMIN E | 10 mg |
| VEGETABLE MAGNESIUM STEARATE | 2.4 mg |
| MICROCRYSTALLINE CELLULOSE | 49.5 mg |
| SIPERNAT (HYDRATED SILICA) | 2.6 mg |
| DIBASIC CALCIUM PHOSPHATE | 10.5 mg |

What is claimed is:

1. A food supplement based on NADH, Octocosonol and Vitamin E, further comprising other vitamins selected from the group consisting of beta carotene, nicotinamide, adenosine and other anti-oxidants selected from the group consisting of grape extract, powdered red wine, resveratrol and lycopene; bioflavonoids selected from the group consisting of from citrus fruit, alpha lypoic acid and carotenoids; selenium yeast, ubidecarenon (Q10 enzyme activator), dry whortleberry extract, reduced glutatione, dry sea pine barl extract, apple vinegar, dry green tea extract, dry elder tree extract, and antocyanines from red oranges.

2. A food supplement according to claim 1, comprising NADH in quantity of 1–15% by weight of the total composition, Octocosanol in a quantity of 1–15% by weight of the total composition, and Vitamin E in a quantity of 2–15% of the total composition.

3. A food supplement according to claim 1, comprising NADH in a quantity of 3–7% by weight of the total composition, Octocosanol in a quantity of 3–7% by weight of the total composition, and Vitamin E in a quantity of 6–13% of the total composition.

4. A food supplement according to claim 1, in the technical form of a tablet coated by a gastrointestinally protective film.

* * * * *